(12) United States Patent
Pashley et al.

(10) Patent No.: US 6,275,049 B1
(45) Date of Patent: Aug. 14, 2001

(54) METHOD AND APPARATUS FOR THE MEASUREMENT OF FILM FORMATION TEMPERATURE OF A LATEX

(75) Inventors: Richard Mark Pashley, Aranda; Marilyn Emily Karaman, Chisholm; Barry William Ninham, Cook, all of (AU)

(73) Assignee: The Australian National University, Australian Capital Territory (AU)

( * ) Notice: Subject to any disclaimer, the term of this patent is extended or adjusted under 35 U.S.C. 154(b) by 0 days.

(21) Appl. No.: 09/023,026

(22) Filed: Feb. 12, 1998

(51) Int. Cl.[7] .......................... G01R 27/08; G01R 27/28; G03G 5/00

(52) U.S. Cl. .......................... 324/693; 324/654; 430/137

(58) Field of Search .................... 324/439, 654, 324/693; 430/137

(56) References Cited

U.S. PATENT DOCUMENTS

| 3,657,640 | * | 4/1972 | Jelinek et al. | 324/30 R |
| 5,140,275 | * | 8/1992 | Schoerner et al. | 324/693 |
| 5,523,959 | * | 6/1996 | Seegmiller | 324/654 |
| 5,644,239 | * | 7/1997 | Huang et al. | 324/439 |
| 5,650,255 | * | 7/1997 | Ng et al. | 430/137 |

* cited by examiner

*Primary Examiner*—Safet Metjahic
*Assistant Examiner*—James Kerveros
(74) *Attorney, Agent, or Firm*—Welsh & Katz, Ltd.

(57) ABSTRACT

Apparatus and methods for determining the minimum film formation temperature of a latex are disclosed based upon the measurement of the conductivity of the latex as the temperature of the latex is varied. By plotting the latex's conductivity and temperature relationship, the minimum film formation temperature is determined.

9 Claims, 4 Drawing Sheets

METHOD AND APPARATUS FOR THE MEASUREMENT OF FILM FORMATION TEMPERATURE OF A LATEX

BACKGROUND OF THE INVENTION

The critical temperature required for a latex coating to form a strong, continuous film is important in the design and use of these coatings. This temperature is known as the minimum film formation temperature (MFFT).

Presently, an optical method is employed to measure the MFFT. The method involves the observation of the clarity of a cast film on a large metal table. A temperature gradient is applied to the table and the position on the table where the film is judged to be clear is noted. The temperature at that point on the table is determined to be the MFFT value. This technique may provide variable, operator dependent results. Another difficulty with this method is that only optically clear latexes can be tested. Pigments and other additives which are known to alter the MFFT cannot be used using this method. Accordingly a method to objectively measure the film formation temperature of a latex is desirable, especially a method which can also be used with pigmented latices.

SUMMARY OF THE INVENTION

One aspect of the present invention is a method for measuring the minimum film formation temperature comprising:

providing a latex;

measuring the initial conductivity (K) of the latex;

measuring the temperature of the latex (T);

heating the latex solution;

measuring the conductivity of the latex while it is being heated;

determining the point in which the conductivity of the latex changes sharply with temperature; and determining the minimum film formation temperature by calculating the maximum point in the curve described by $(+/-)d^2K/dT^2$ versus temperature.

A second embodiment of the present invention provides apparatus for the film formation temperature a latex. The apparatus comprises:

a container suitable for holding a latex solution;

means for removing water from the latex solution via osmotic suction;

means for measuring the conductivity of a latex;

means for measuring the temperature of a latex;

means for modifying the temperature of a latex provided in the container; and means for determining the minimum film formation temperature by calculating the maximum point in the curve described by $(+/-) d^2K/dT^2$ temperature.

The new method is based upon the discovery that the film formation properties of latex materials, such as paints and other coatings, can be dried in a controlled manner using osmotic suction to the point where latex becomes critically dependent on temperature. At the MFFT value the latex particles soften and deform, which in turn changes the solid drying curve. Surprisingly, we have also discovered that the conductivity of the latex is also sensitive to this same transition point and is an ideal parameter for monitoring this change.

As used throughout the specification, conductivity of the latex will be used to determine the MFFT. Those with skill in the art will realize that other electrical parameters could be used to detect the change in behavior such as dielectric constant, and these parameters are understood to be within the scope of the present invention. One reason the present invention employs conductivity in the description of the invention is the relative easy in which conductivity can be measured.

The conductivity of latex solutions is caused by the presence of free ions in the latex between the particles while under osmotic suction. At the MFFT point the deformation of the latex particles reduces the pore size and ion conductivity between the particles. Some latex samples demonstrate a sharp increase in conductivity with temperature. The conductivity change in the latex solution typically occurs at a solids level of from 60–85 weight percent, preferably from 65 to 80 weight percent and in a highly preferred embodiment at 75 weight percent by weight solids. This increase is probably due to the release of ionic materials from the interior of the latex particles at the softening temperature. The MFFT value is therefore determined as a sharp change in conductivity as the temperature of the latex sample is increased across the transition range when the film is formed. Therefore by plotting the conductivity of a latex solution at various temperatures it is possible to calculate the rate of change of the conductivity of the latex versus the rate of change of the temperature (dK/dT) versus temperature. This is the first also done by calculating the first derivative of the conductivity versus temperature curve.

By calculating the second derivative of the conductivity versus temperature $(+/-d^2K/dT^2)$ versus temperature, the MFFT can be calculated. The maximum in this curve is at the minimum film formation temperature. This result is provided by fundamental principles of calculus. The ability to calculate the rate of change of the conductivity per the rate of change of temperature by taking a derivative is known by those with skill in the art.

The direction of the transition may be altered by the frequency at which the conductivity is measured. The present invention and the accompanying examples were conducted at 1000 HZ, although those with skill in the art could easily vary the frequency employed. The transition may be altered or enhanced by variation of the frequency without departing from the scope of the present invention.

DETAILED DESCRIPTION OF THE INVENTION

Figure 1A:
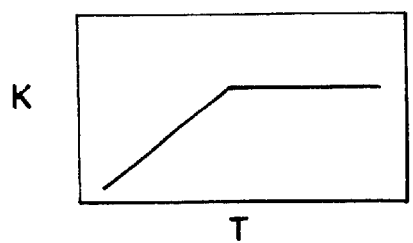
FIG. 1A represents a typical conductivity curve.
Figure 1B:
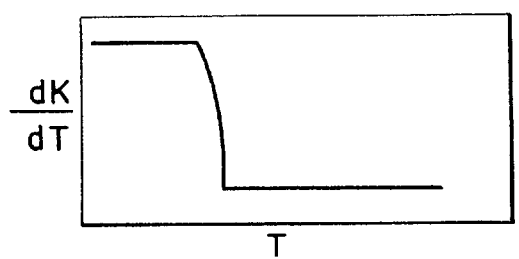
FIG. 1B is a first derivative curve calculated from FIG. 1A.
Figure 1C:
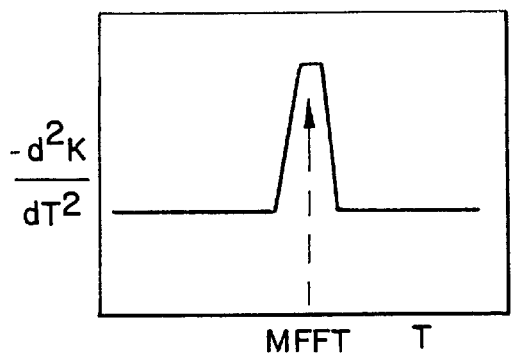
FIG. 1C is a second derivative curve calculated from FIG. 1A.

Three representative curves are presented in FIG. 1. FIG. 1A depicts a typical conductivity versus temperature curve. FIG. 1B depicts the first derivative calculated from the conductivity versus temperature curve. The curve describes the conductivity rate of change divided by the rate of change of the temperature plotted versus temperature. FIG. 1C depicts the second derivative calculated from the conductivity versus temperature curve. The negative of the second derivative is provided to have positive number. As depicted in the figure, the maximum point of the curve is the minimum film formation temperature.

Figure 2A:
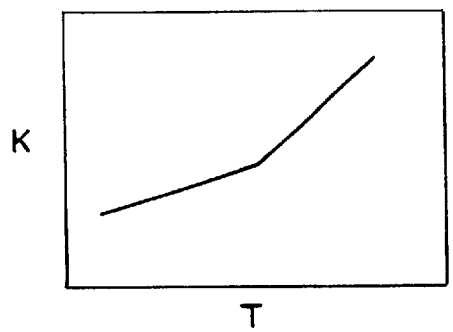
FIG. 2A, 2B and 2C are reverse transitions of FIGS. 1A, 1B, and 1C, respectively.
Figure 2B:
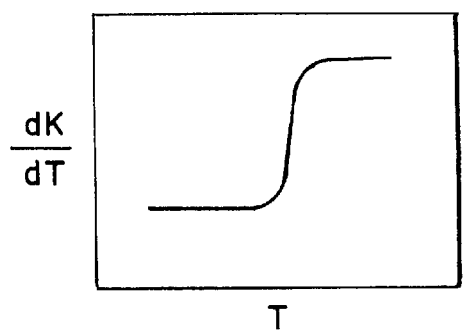
Figure 2C:
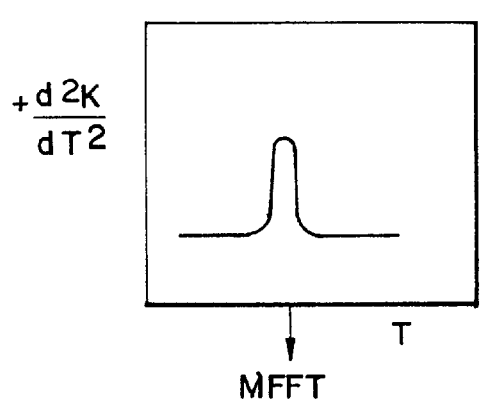

FIGS. 2A, 2B and 2C are provided to demonstrate the reverse transition of the curves found in FIG. 1. These curves may be generated depending on the latex sample provided. If the sample provides these curves it will be necessary to calculate the $+d^2K/dT^2$ in order to determine the minimum film formation temperature.

Figure 3A:
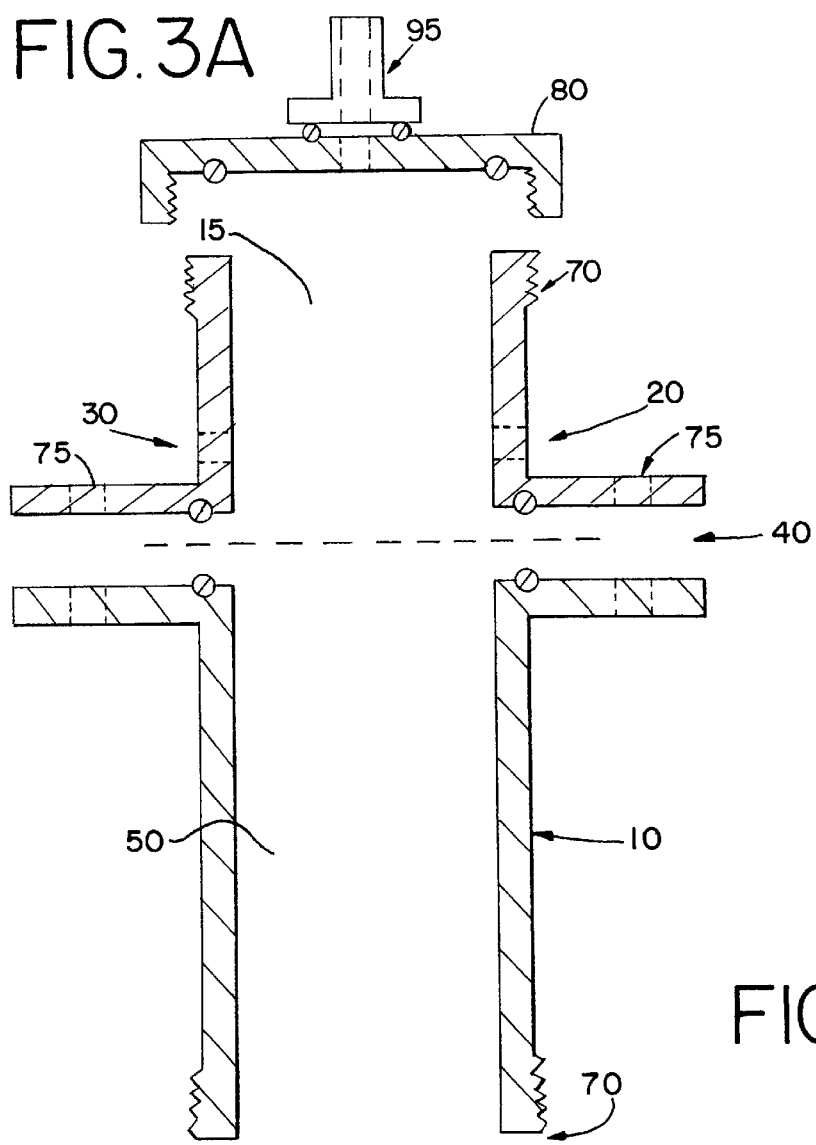
FIG. 3A is a schematic of a cell body for drying and maintaining a latex sample.

FIG. 3A is a schematic of the cell body (10) used to dry and maintain the latex. The cell body is constructed of a suitable material such as metals, plastics or ceramics. Suitable metals include aluminum, copper and iron, and alloys such as steel, stainless steel, brass and bronze. Preferably the cell is constructed of a non-corrosive material, such as stainless steel. The cell has an osmotic membrane (40).

The cell can be used with a wide range of membrane materials. The membrane materials affects the rate of drying and whether any additives are leached out with water. For example, use of a reverse osmosis membrane (e.g. cellulose acetate) will allow drying to occur at a low rate and will only allow water to pass through the membrane. Low molar mass solutes such as salts and additives such as ethylene glycol will not be withdrawn form the latex solution.

Use of dialysis membrane (e.g. with a molar mass cut-off of 1000 gram mole$^{-1}$) enables much faster drying and has been used successfully. However, some loss of low molar mass solutes may occur. The loss of the solutes does not appear to alter the observed MFFT value.

Referring to FIG. 3A, in the upper portion of the cell body a cavity is provided (15) in which the latex is provided. In the lower portion of the cell body on the side opposite of the latex solution a cavity (50) is provided to hold a solution of PVP. PVP is employed because accurate osmotic pressure values are available in the literature, such as the PVP osmotic pressure data given in: H. Link, European Polymer Journal, 1971, vol. 7, 1411–1419. PVP is also desirable because it is very water soluble and is available with a wide range of average molar mass values. The polymer solution generates an osmotic suction pressure acting on the water in the latex through the semi-permeable membrane.

Rapid, convenient drying was obtained using 10,000 gram-mole$^{-1}$ PVP with a dialysis membrane with a molar mass cut off of 1,000 gram-mole$^{-1}$. That is the membrane will only allow passage of low molar mass solutes less than 1,000 gram-mole$^{-1}$.

An alternative method would be to use sugar or salt solution to generate an osmotic suction across a reverse osmosis membrane. A reverse osmosis membrane will allow only water to pass. These membranes are, however, significantly slower at water transfer, although this can be compensated to some extent by the use of Much higher osmotic pressures.

Apertures for a conductivity electrode (30) and thermistor (20) are also provided. The cell body is preferably threaded on both the top and bottom of the cell body (70) in order to facilitate the filling, emptying and cleaning of the cell body. Gasketing material (80) such as rubber o-rings are provided to minimize leakage of the fluids from the cell body. Ports (95) with a central cavity (96) are provided to facilitate free transfer of water across the membrane. Fastens such as screws, (75) are preferably provided in order to facilitate the easy assembly and disassembly of the cell body.

Figure 3B:
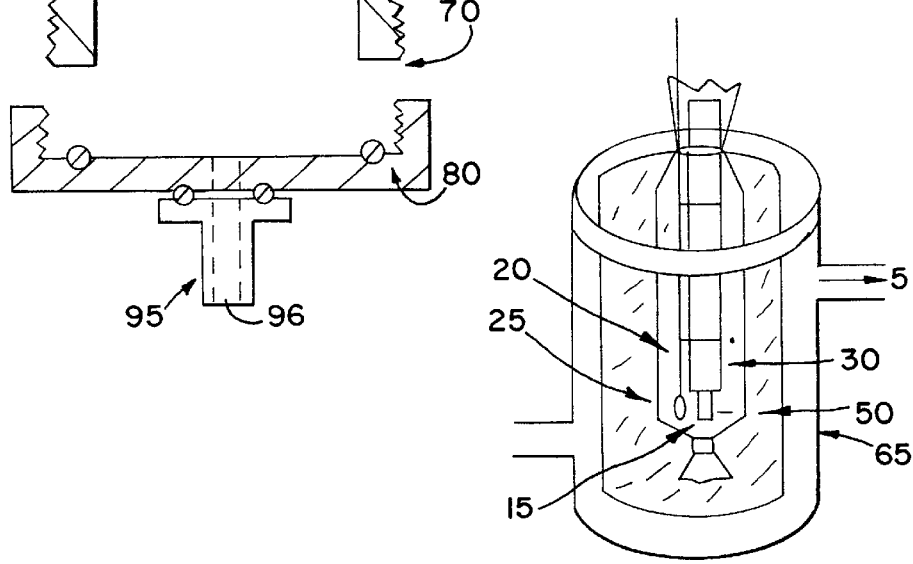
FIG. 3B is depiction of a structure which uses a rubber tubing to contain a latex sample.

In an alternative embodiment of the invention, the cell body is replaced with a piece of dialysis tubing. FIG. 3B illustrates an arrangement which employs a piece of tubing in order to contain a latex.

Suitable tubing, such as tubing used in dialysis treatments (25) is employed. The latex solution (15) is added to the tubing. PVP or other suitable solutions (50) is provided to the chamber (65) in which the dialysis tubing is immersed. Means for measuring the temperature, such as a thermistor (20); and a conductivity measuring device, conductivity electrode (30) are provided within the tubing.

The tubing and the PVP solution are contained in a jacketed cell (5). The jacketed cell contains an annular space in which a heat transfer fluid, such as water is provided. For simplicity the means for modifying the temperature of the heat transfer fluid, pumps, associated equipment for the collection of the conductivity and temperature measurements and other apparatus are omitted.

Figure 4:
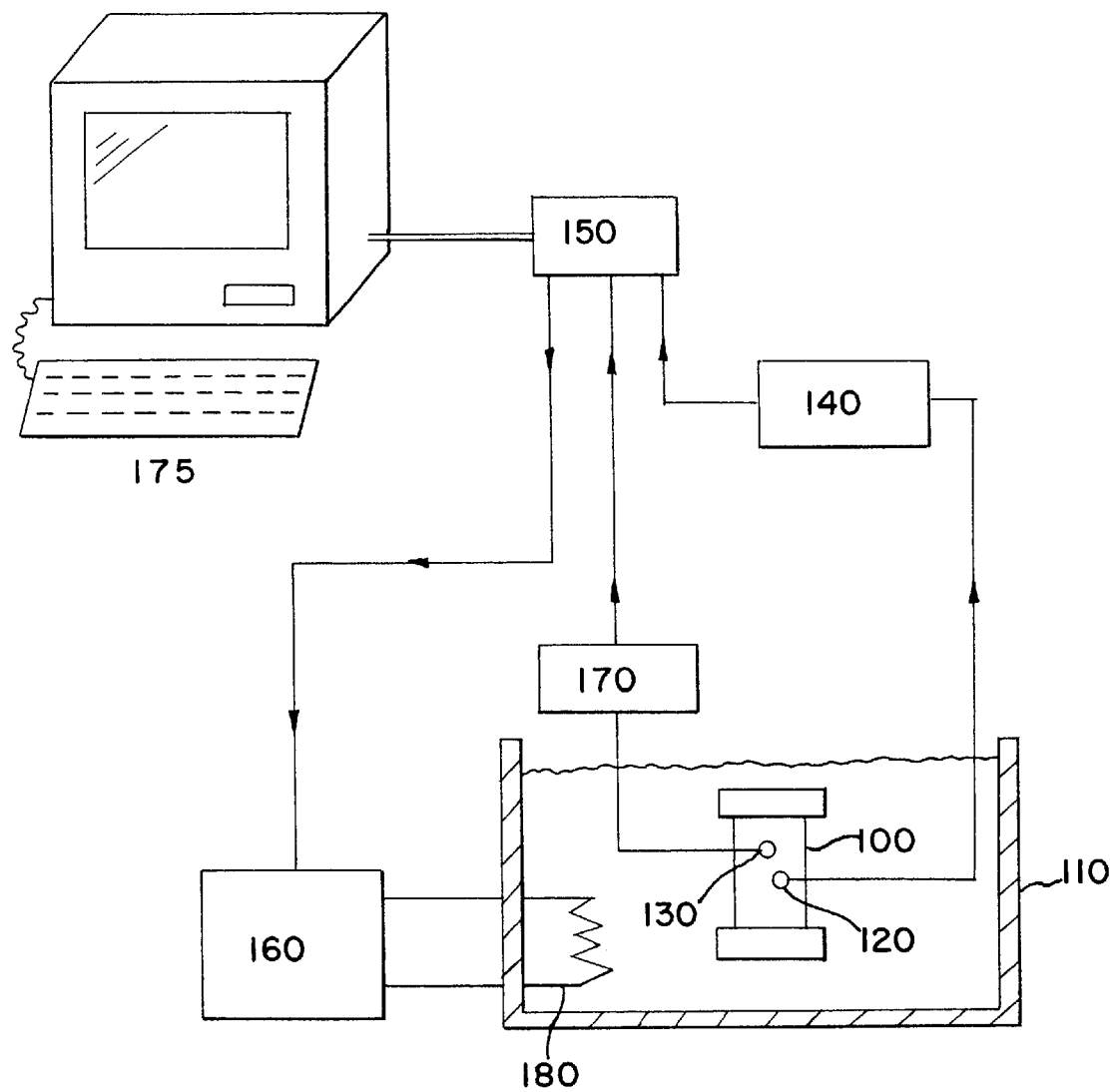
FIG. 4 is a diagram of equipment for measuring minimum film formation temperature.

FIG. 4 is a simplified diagram of the equipment employed in the measurement of the minimum film formation temperature. The chamber (100) containing the latex is placed in the heat transfer fluid, a water bath. The chamber has apertures suitable for connecting a thermistor (120) and conductivity measurement device (130). The thermistor is preferably connected to a temperature display (140) which in turn is connected to a digital analog interface (150). The digital analog interface is also connected to a conductivity meter (170). The digital analog interface is also connected to an electronic device (160) capable of measuring and modifying the temperature of the water bath. Means for both heating and cooling the water bath is preferably provided. A computer device (175) is preferably provided to both collect the conductivity and temperature data, as well as controlling and modifying the temperature of the water bath. In a preferred embodiment the computer is programmed to provide a print out of the information depicted in FIGS. 1 and 2, thereby providing the minimum film formation temperature. A computer with a 486 processor and the necessary associated software suitable for the task of collecting the required data and modifying the temperature of the water bath. The software employed was Labview, written by National Instruments, Austin, Tex.

The method of the present invention is performed as follows. The initial conductivity value of the latex sample is obtained and the data is recorded, preferably the data is transferred to a computer. The water bath remains at the specified temperature, typically about 2° C. until the measured conductivity, with drying occurring, reaches a predetermined value.

The use of conductivity as a convenient and monitor of latex solids has been examined using Bruggeman equations (Ann. Phys., 24, 636, 1935 and 'Surfactants in Solution', ed. Mittal and Lindeman, vol. 3 1982) on a range of latex samples. The standard form of the Bruggeman equation is:

$$k=k_m(1-\phi)^{1.5}$$

where k and $k_m$ are the conductivities of the latex solution and the continuous (i.e. permeate) phase, respectively, and ø is the volume fraction of the dispersed phase. The equation is most suitable for a monodisperse solution of non-conducting spheres. Preferably the predetermined value corresponds to the estimated conductivity value of approximately 75% solids in the latex.

Once this estimated conductivity is obtained the computer program begins to ramp the temperature of the water bath at a continuous rate which is specified in the computer program. Typically the temperature of the water bath is increased at a rate of from about 1° C./hour and more preferably at a rate of 3° C./hour. Typically, the temperature of the water bath is raised to approximately 35° C. while continuously monitoring the temperature and conductivity of the latex.

When the temperature of the bath reaches 35° C. it is then maintained at this temperature until the temperature of the latex reaches approximately 30° C. At this latex temperature the test is concluded and the water bath is cooled and the sample removed.

The initial conductivity of the latex' solution is measured by the computer. The computer will then determine the conductivity of the latex solution achieved during osmotic drying at constant temperature. In addition, measurement of the initial latex conductivity, where percent solids is known, allow the calculation of both the permeate (continuous phase conductivity) and the conductivity expected at 75% by weight solids—where it is desirable to begin the MFFT run for each latex sample. The Bruggeman equation should be valid up to about 75% solids, at which stage the latex particles will begin to come into physical contact with each other. When the conductivity at 75%, solids value is reached the temperature ramp for the latex is started via the temperature bath. The temperature is then increased until it reaches the final desired temperature. The MFFT is then calculated from the curve by determining the rate of change of conductivity per rate of change of temperature versus temperature.

The present invention may be used to measure the minimum film formation temperature of a latex capable of forming a film. Such latices are suitable for use in a paints, lacquers, shellacs, stains and the like. As noted above, one advantage of the present invention is that the film forming substance may be pigmented as well as non-pigmented.

The following example are illustrative of the present invention. The following equipment was employed in the examples.

CDM 80 conductivity meter, platinum electrode;

temperature meter and thermistor;

Julabo FIO refrigerated water bath;

Jacketed glass cell;

dialysis tubing (benzoylated cellulose) 1,000 molecular weight cutoff, tubing; Sigma Chemical Co.

40% by weight polyvinyl pyrrolidone solution of approximately 10,000 molecular weight, Aldrich Chemical Co.;

486 IBM personal computer;

Software written for this application which stores conductivity and data temperature at a rate of approximately 3 data points per seconds, Labview, National Instruments, Austin, Tex.

EXAMPLE 1

Apparatus and Method for Performing the Invention Using Tubing

A 40% weight polyvinyl pyrrolidone (PVP) solution (approximately 10,000 molecular weight) was prepared and transferred to a jacketed cell which is placed in a refrigerated water bath at 2° C. Plastic tubing suitable for use in dialysis, was softened by placing in water, wiped dry and one end was sealed. The tubing was filled with a precooled (about 2° C.) latex sample and a conductivity electrode and thermistor were placed in the dialysis tubing and then the tubing was sealed. The tubing containing the sample was then placed into the cooled PVP solution.

Figure 5:
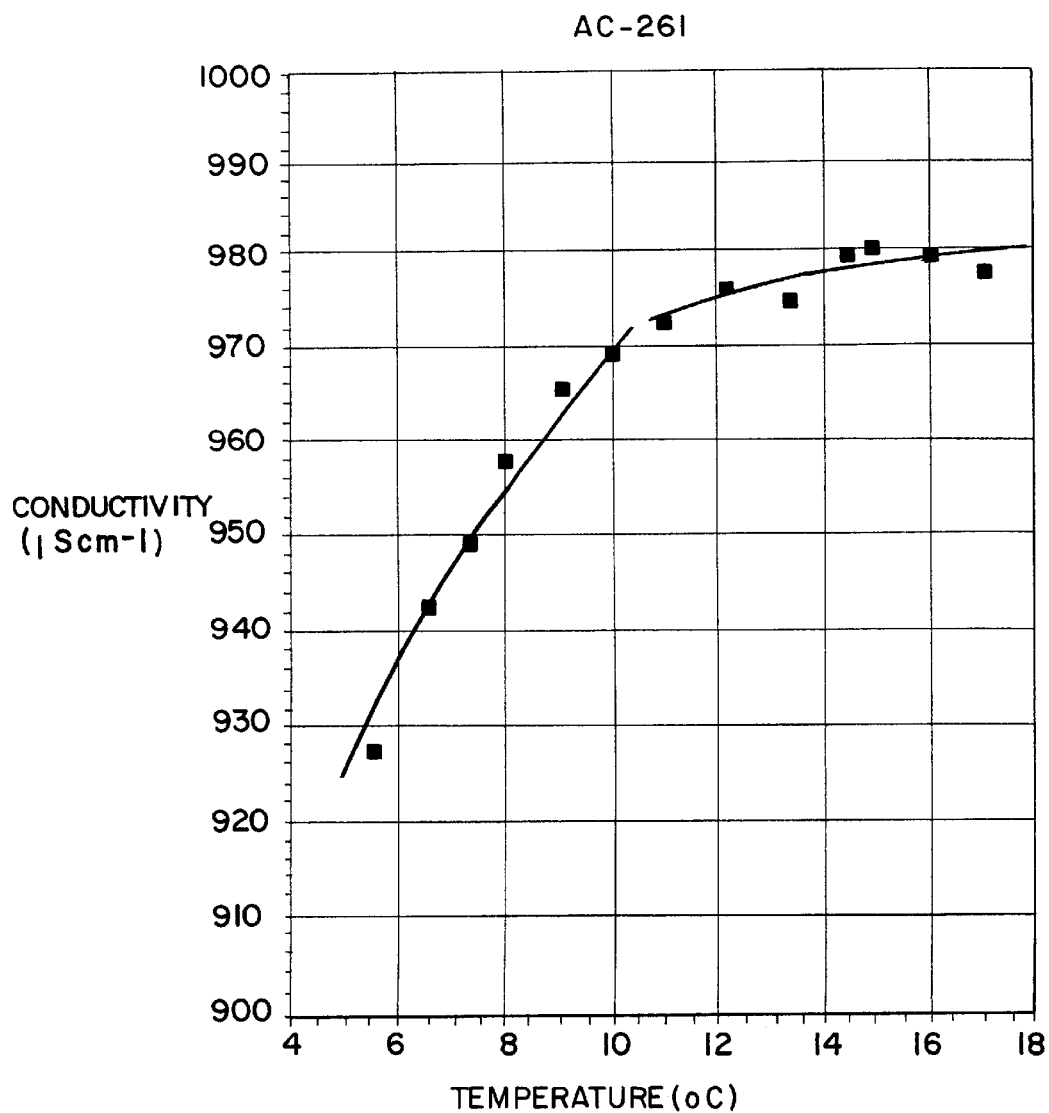
FIG. 5 is a graph of conductivity vs. temperature for a latex sample.

A sample of Primal® AC-261 acrylic latex (Rohm and Haas Company) was tested in the apparatus described hereinabove. After an initial conductivity measurement the temperature of the water bath was ramped at a rate of 3° C. per hour to a final temperature of 30° C. At the start of the temperature ramp the response between conductivity and temperature is linear. However as the latex solution approaches the MFFT temperature the response to the slope decrease rapidly. This is believed to be caused by the flattening of the latex particles and the reduction of pore size. The conductivity versus temperature curve is provided in FIG. 5. For the AC-261 sample the MFFT occurred at a temperature of 10.5° C.

The minimum film formation temperature was confirmed via testing of the sample by the traditional mechanical method.

EXAMPLE 2

Comparison of Bruggeman Equation Results to Observed Results

Various latices were used to test the results provided by the Bruggeman equation and the results obtained by measuring the latex. The conductivity of the continuous phase was obtained via high pressure filtration of each latex sample through 6–8,000 molar mass cut-off dialysis membrane.

| Latex Sample | conductivity in mS/cm* | | ∅ (meas)** | ∅(calc)*** |
|---|---|---|---|---|
| | latex | permeate | | |
| 1 | 1.32 | 3.06 | 0.46 | 0.43 |
| 2 | 1.87 | 5.40 | 0.47 | 0.51 |
| 3 | 3.00 | 8.05 | 0.50 | 0.48 |
| 4 | 2.55 | 7.35 | 0.50 | 0.51 |

*mS/per centimeter refers to milli Siemen per cm. (A Siemen is an ohm$^{-1}$)
**measured
***calculated The results demonstrate that the standard Bruggeman equation is applicable to these samples and suggests that conductivity can be used quantitatively as a monitor of latex solids.

We claim:

1. A method for determining the minimum film formation temperature of a latex comprising:

providing latex, measuring the initial conductivity (K) of the latex;

measuring the temperature of the latex (T);

heating the latex;

measuring the conductivity of the latex while it is being heated to obtain a plurality of values K;

measuring the temperature of the latex while it is being heated to obtain a plurality of values T;

graphing the values K versus T to prepare a curve;

graphically taking the first derivative of the curve;

graphically taking te second derivative of the, first derivative curve; and determining the minimum film formation temperature by determining a maximum point in the curve described by the second derivative curve.

2. The method of claim 1 wherein the latex additionally contains a pigment.

3. The temperature of the method of claim 1 wherein the latex is uniformly increased at the rate of 3° C. per hour.

4. The method of claim 3 wherein the latex contains a pigment.

5. The method of claim 1 wherein the conductivity of the latex is measured when the latex solution contains from 65 to 80 percent by weight solids.

6. Apparatus for measuring the film formation temperature of a latex, said apparatus comprising:

a container suitable for holding a latex solution;

means for measuring the conductivity (K) of a latex;

means for measuring the temperature (T) of a latex;

means for modifying the temperature of a latex provided in the container; and means for graphically determining a second derivative curve of a K versus T graph and the minimum film formation temperature by determining a maximum point in the second derivative curve.

7. The apparatus of claim 6 wherein the container is a piece of tubing.

8. The apparatus of claim 6 wherein the means for measuring the temperature of the latex is a thermistor.

9. The apparatus of claim 6 wherein the means for measuring the conductivity of the latex is a conductivity electrode.

\* \* \* \* \*